(12) United States Patent
Shields et al.

(10) Patent No.: US 9,958,673 B2
(45) Date of Patent: May 1, 2018

(54) PROTECTED LENS COVER PLATE FOR AN OPTICAL METROLOGY DEVICE

(71) Applicant: Nanometrics Incorporated, Milpitas, CA (US)

(72) Inventors: Jason Robert Shields, Pleasanton, CA (US); Nir Ben Moshe, Cupertino, CA (US); Andrew J. Hazelton, San Carlos, CA (US)

(73) Assignee: Nanometrics Incorporated, Milpitas, CA (US)

( * ) Notice: Subject to any disclaimer, the term of this patent is extended or adjusted under 35 U.S.C. 154(b) by 134 days.

(21) Appl. No.: 14/809,056

(22) Filed: Jul. 24, 2015

(65) Prior Publication Data

US 2016/0033763 A1 Feb. 4, 2016

Related U.S. Application Data

(60) Provisional application No. 62/030,537, filed on Jul. 29, 2014.

(51) Int. Cl.
*G01N 21/15* (2006.01)
*G02B 27/00* (2006.01)
(Continued)

(52) U.S. Cl.
CPC ......... *G02B 27/0006* (2013.01); *G01N 21/15* (2013.01); *G01N 21/9501* (2013.01);
(Continued)

(58) Field of Classification Search
USPC .......................................... 356/237.1–241.6
See application file for complete search history.

(56) References Cited

U.S. PATENT DOCUMENTS 3,495,259 A * 2/1970 Hertel ................ G02B 27/0006
2/435
4,443,072 A 4/1984 Ballard
(Continued)

FOREIGN PATENT DOCUMENTS

EP 0 456 202 A2 11/1991
GB 2 022 993 A 12/1979
(Continued)

OTHER PUBLICATIONS

Machine translation in English of Abstract for TW 1340241 B visited at www.espacenet.com on Nov. 4, 2016, one page.
(Continued)

*Primary Examiner* — Shawn Decenzo
*Assistant Examiner* — Jarreas C Underwood
(74) *Attorney, Agent, or Firm* — Silicon Valley Patent Group LLP

(57) ABSTRACT

A cover plate or lens for an optical metrology device that is positioned under a wafer during measurement is protected with a purge device. The purge device may include a ring that extends around a periphery of the cover plate or lens. The ring includes a plurality of apertures through which a purge gas or air is expelled over the surface of the cover plate or lens. Additionally or alternatively, one or more heating elements may be provided that extend around the periphery of the cover plate or lens. The heating elements heat the cover plate above a dewpoint temperature of contaminant vapor. A heat sensor may be used to monitor the temperature of the cover plate to control the heating elements and/or to compensate for optical changes of the cover plate caused by heating during measurement of a wafer.

10 Claims, 2 Drawing Sheets

(51) Int. Cl.
  *G01R 31/28* (2006.01)
  *G01R 31/302* (2006.01)
  *G01N 21/95* (2006.01)

(52) U.S. Cl.
  CPC ....... *G01R 31/2831* (2013.01); *G01R 31/302* (2013.01); *G01N 2021/151* (2013.01); *G01N 2201/068* (2013.01)

(56) References Cited

U.S. PATENT DOCUMENTS

| | | | |
|---|---|---|---|
| 5,352,636 A * | 10/1994 | Beinglass | C23C 16/0218 148/DIG. 17 |
| 5,611,886 A * | 3/1997 | Bachman | B05C 11/08 118/52 |
| 5,931,721 A * | 8/1999 | Rose | B08B 7/0092 451/39 |
| 6,135,862 A * | 10/2000 | Ukai | B23Q 11/0042 409/136 |
| 6,159,299 A | 12/2000 | Koai et al. | |
| 6,274,878 B1 * | 8/2001 | Li | H01L 21/67259 250/222.1 |
| 6,389,886 B2 | 5/2002 | Daniels et al. | |
| 6,541,376 B2 * | 4/2003 | Inada | G03F 7/162 438/618 |
| 6,628,397 B1 | 9/2003 | Nikoonahad et al. | |
| 6,795,164 B2 * | 9/2004 | Hoogenraad | G03F 9/7011 355/53 |
| 6,986,636 B2 * | 1/2006 | Konig | H01L 21/68 414/754 |
| 7,138,640 B1 * | 11/2006 | Delgado | G01N 21/15 250/372 |
| 7,420,681 B1 | 9/2008 | Wang et al. | |
| 7,656,519 B2 * | 2/2010 | Meeks | G01B 11/065 356/237.2 |
| 7,755,764 B2 | 7/2010 | Kwak et al. | |
| 8,125,654 B2 * | 2/2012 | Benvegnu | B24B 37/013 356/630 |
| 8,216,382 B2 * | 7/2012 | Shindo | B08B 7/0042 134/1 |
| 8,274,743 B2 * | 9/2012 | Scaggs | G02B 7/028 359/641 |
| 8,334,222 B2 * | 12/2012 | Gotou | H01L 21/02049 257/E21.001 |
| 8,718,810 B2 * | 5/2014 | Benvegnu | B24B 37/013 700/121 |
| 9,234,280 B2 * | 1/2016 | Shimizu | C30B 25/12 |
| 2002/0098283 A1 * | 7/2002 | Gurer | B05C 5/0208 427/240 |
| 2002/0149774 A1 | 10/2002 | McAninch | |
| 2004/0207836 A1 * | 10/2004 | Chhibber | G01N 21/4738 356/237.4 |
| 2005/0252752 A1 | 11/2005 | Fielden et al. | |
| 2009/0084409 A1 * | 4/2009 | Okura | B08B 3/02 134/21 |
| 2009/0122293 A1 * | 5/2009 | Shibazaki | G03F 7/70716 355/73 |
| 2010/0024887 A1 * | 2/2010 | Williams | F15D 1/00 137/2 |
| 2010/0124610 A1 * | 5/2010 | Aikawa | C23C 16/4584 427/255.28 |
| 2011/0253044 A1 * | 10/2011 | Tam | C23C 16/45519 118/666 |

FOREIGN PATENT DOCUMENTS

| | | |
|---|---|---|
| TW | 564944 U | 12/2003 |
| TW | I340241 B | 4/2011 |
| WO | WO 2005/102544 A1 | 11/2005 |

OTHER PUBLICATIONS

International Search Report and Written Opinion dated Oct. 7, 2015 for International Application No. PCT/US2015/042312 dated Jul. 27, 2015 by Nanometric Incorporated, 12 pages.

* cited by examiner

PROTECTED LENS COVER PLATE FOR AN OPTICAL METROLOGY DEVICE

CROSS REFERENCE TO RELATED APPLICATIONS

This application claims priority under 35 USC 119 to U.S. Provisional Application No. 62/030,537, entitled "Protected Lens Cover Plate For An Optical Metrology Device," filed Jul. 29, 2014, which is incorporated herein by reference in its entirety.

BACKGROUND

To improve process control for some semiconductor manufacturing processes, integrated metrology (IM) modules are attached to the process tool and used to measure and quickly provide feedback for real-time control of the process. A typical IM module is built with the same form factor as a loadport, allowing it to be attached to the process tool EFEM (equipment front end module) in place of a loadport. In this case, the wafer handling robot, which is a part of the EFEM, can easily load wafers into the IM module. Typically, there is an open port between the IM and the EFEM, allowing the robot to freely load wafers into the IM.

In order to fit into the form factor of a loadport, the IM needs to be fairly compact. While typical stand-alone metrology tools may have a fan filter unit (FFU) to filter out particles, condition the air temperature, and provide laminar downflow, there is generally not enough space in the IM to include this FFU, so the conditioned air is provided by the EFEM.

In some cases, the metrology instrument in the IM module may be a spectroscopic reflectometer (SR), but other types of metrology instruments may be used. Generally, the spectroscopic reflectomer measures the reflectivity of the wafer across a range of wavelengths. This information can be used to derive, for example, a film thickness of a thin film on the surface of the wafer, or the critical dimension (CD) of a device on the wafer. In some implementations, the wafer is loaded face down into the IM module, with the optics of the metrology device located below the wafer. The optics may move under the wafer to measure desired locations on the wafer. In some implementations, both the optics and the wafer may move, or only the wafer may move.

With the IM module directly connected to the process tool, wafers may be loaded into the IM module immediately after they leave the processing module. Measuring wafers immediately after leaving the processing module allows for rapid process feedback, but in many cases remnants from the processing are still present on the wafer, which may affect the performance of the metrology device. For example, in the case of an etch process, the etch gases may be absorbed by the processed wafer, and slowly leak out (outgas). For example, in the case of polysilicon etch, bromic acid (hydrogen bromate, HBrO3) is sometimes used. When wafers are measured immediately after the etch process, the etch gases may leak out into the environment of the IM module.

The introduction of process remnants, such as etch outgas, may affect the performance of the optical metrology device in the IM module. For example, gases that are used to etch silicon may etch the lens of the metrology tool or the window between the wafer and the lens, thereby changing the optical properties of the lens or window. Other gases outgassed by the wafer may condense on the surface of the lens or window which will also adversely change the optical properties of the lens or window.

SUMMARY

A cover plate or lens for an optical metrology device that is positioned under a wafer during measurement is protected with a purge device. The purge device may include a ring that extends around a periphery of the cover plate or lens. The ring includes a plurality of apertures through which a purge gas or air is expelled over the surface of the cover plate or lens. Additionally or alternatively, one or more heating elements may be provided that extend around the periphery of the cover plate or lens. The heating elements heat the cover plate above a dewpoint temperature of contaminant vapor. A heat sensor may be used to monitor the temperature of the cover plate to control the heating elements and/or to compensate for optical changes of the cover plate caused by heating during measurement of a wafer.

DETAILED DESCRIPTION

The introduction of process remnants, such as etch outgas, may affect the performance of an optical metrology device, such as those in an integrated metrology module. For example, gases that are used to etch silicon may be outgassed by the wafer after processing. When a wafer is inserted into the environment of the optical metrology device soon or immediately after processing, the etching gases that are outgassed by the wafer may etch a lens or window of the optical metrology device positioned below the wafer, thereby changing the optical properties of the lens or window. Other gases, such as hydrogen bromate (HBrO3) may condense on the surface of the lens or window thereby affecting the optical properties of the lens or window.

By way of example, some optical metrology devices may sample a reference chip that is positioned below the window separating the optics and the wafer, while the wafer being measured is held above the window. In such a configuration, process remnants introduced into the IM module by the processed wafer will affect the optical properties of the window, but not the reference chip, thereby adversely affecting the measurement of the wafer. Additionally, even if a reference wafer is held above the window, e.g., the reference wafer may be loaded into the system in place of a sample wafer, the optical properties of the window may change between sampling the reference wafer and measuring the wafer due to process remnants introduced into the IM module. Further, the changes to the optical properties of the window caused by process remnants introduced into the IM module by a processed wafer may be non-uniform across the window or lens, thereby adversely affecting the performance of the optical metrology device.

Figure 1:
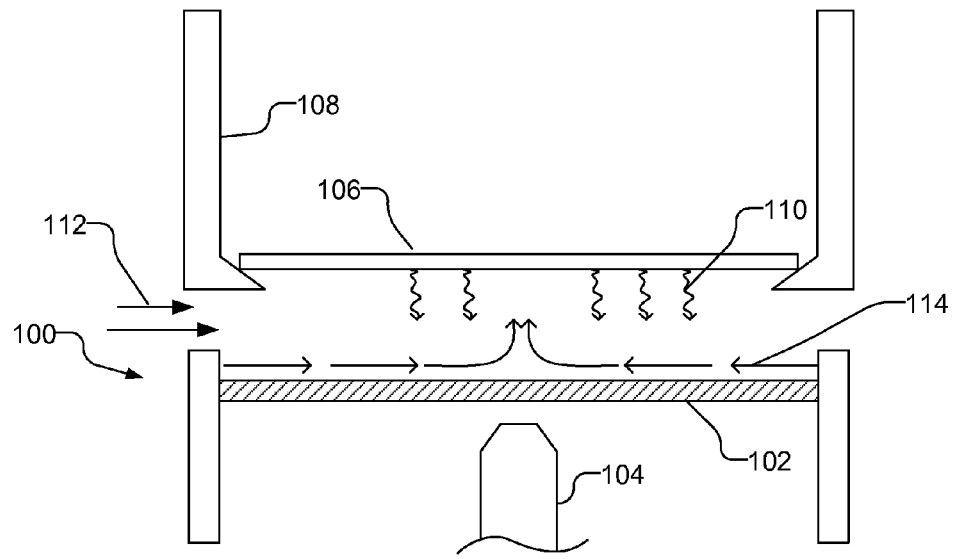
FIG. 1 illustrates a side view of a purge device that protects a lens cover plate for optics of an optical metrology device from process remnants of a processed wafer.

FIG. 1 illustrates a purge device 100 that protects the lens cover plate 102 for the optics 104 of an optical metrology device from process remnants of a processed wafer 106. The wafer 106 is shown supported by arms 108 at the edges of the wafer 106, facing down towards the optics 104. In front of the optics 104, i.e., between the optics 104 and the wafer 106 is a large, clear cover plate 102. The cover plate 102 may be larger than the diameter of the wafer to allow the optics 104 to move freely and measure any location on the wafer 106. In the configuration of FIG. 1, the wafer 106 and the cover plate 102 are exposed to the process remnants, illustrated by arrows 110. While the cover plate 102 protects the delicate optics 104 of the optical metrology device from the process remnants 110, the cover plate 102 is in the optical measurement path and, accordingly, any change in the optical properties of the cover plate 102 will affect the measurement of the wafer 106. For example, process remnants, such as gases used to etch silicon may etch the cover plate 102, changing its surface properties. Additionally, process remnants may condense on the surface of the cover glass thereby changing the optical property of the cover glass.

It should be understood that while a cover plate 102 is illustrated in FIG. 1 as separate from the optics 104, the cover plate 102 may be part of the optics 104. For example, the cover plate 102 may be a lens in the optics 104.

As illustrated in FIG. 1, in some tools an air flow 112 may be introduced. By way of example, in some integrated metrology modules, air 112 may be drawn into the module from the fab through a filter unit in the EFEM. The air 112, for example, may be circulated within the integrated metrology module for temperature and particle control within the tool. The air 112, however, may come into contact with process remnants 110 and, thus, may be characterized as "dirty" air. In order to protect the cover plate 102 from the process remnants 110 that are directly outgassing from the wafer 106 or that may be circulating within the "dirty" air 112, a clean air or gas flow (e.g., clean, dry air or dry nitrogen) is introduced with the purge device 100 in a ring around the perimeter of the cover plate 102. Purge air flow 114 introduced at the periphery of the cover plate 102 by the purge device 100 is controlled, e.g., by placement and orientation of apertures in the purge device 100 as well as pressure and flow rate of the purge air, to cover the entire surface of the cover plate 102, thereby preventing process remnants 110 from contacting the cover plate 102.

Figure 2:
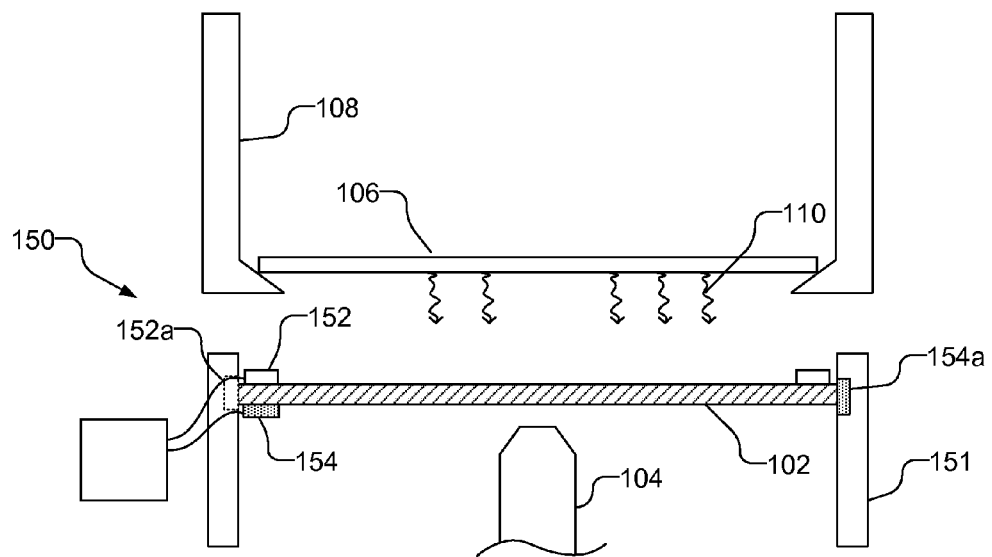
FIG. 2 illustrates a side view of a heating device that is used to prevent condensation on a lens cover plate.

FIG. 2 illustrates side view of a heating device 150 that is used to prevent condensation on the cover plate 102 for the optics 104 of an optical metrology device. For example, where condensation of vapor, such as HBrO3, that is outgassed from the wafer 106, the heating device 150 may be used to prevent condensation from occurring on the cover plate 102 to maintain the optical properties of the cover plate 102. As illustrated, the heating device 150 may include one or more heating elements 152 positioned around the periphery of the cover plate 102 at positions that are not between the optics 104 and the wafer 106, so as to not interfere with the measurement of a wafer 106. The heating elements 152 may heat the cover plate 102 above the dewpoint temperature of the contaminant vapor, such as HBrO3 vapor. At temperatures greater than the dewpoint temperature, the rate of evaporation is higher than the rate of condensation, and, as a result, no condensate collects on the cover plate 102. Additionally, the heating device 150 may include a temperature sensor 154, as illustrated on the bottom of the cover plate 102. This temperature sensor 154 may be used as part of a feedback control loop via controller 156 to maintain the cover plate 102 at a fixed desired temperature. Alternately or additionally, since the change in temperature may change the optical properties of the cover plate 102, data from the temperature sensor 154 may be used to compensate for optical changes to the cover plate 102 due to temperature. If desired, as illustrated with dotted lines, one or both of the heating element 152a and temperature sensor 154a may be located on the support 151 for the cover plate 102, as opposed to being located directly on the cover plate 102, and may heat the cover plate 102 or sense the heat from the cover plate 102 via conduction.

Figure 3:
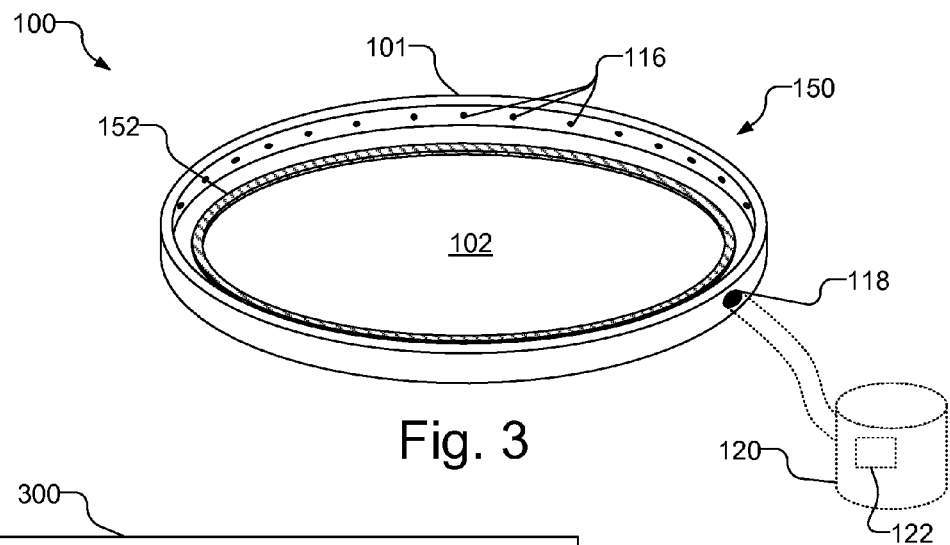
FIG. 3 illustrates a perspective view of a combined purge device and heating device with the lens cover plate.

FIG. 3 illustrates a perspective view of a combined purge device 100 and heating device 150 with the cover plate 102. As can be seen, the purge device 100 includes a ring element 101 that includes a plurality of apertures 116 that extends around the periphery of the cover plate 102 to direct the air flow over the cover plate 102. As illustrated, the ring element 101 of the purge device 100 may include an input port 118 through which the purge air or gas supply 120 is provided. A flow controller 122 may be coupled to the gas supply 120 or the purge device 100 to control the flow of air or gas. The heating element 152 is also illustrated as extending around the periphery of the cover plate 102. If desired, the heating element 152 may be a single heating element or a plurality of separate heating elements positioned at different locations on the cover plate 102 or on the support for the cover plate 102. The temperature sensor 154 may be positioned under the cover plate 102 and is not shown in FIG. 3.

Figure 4:
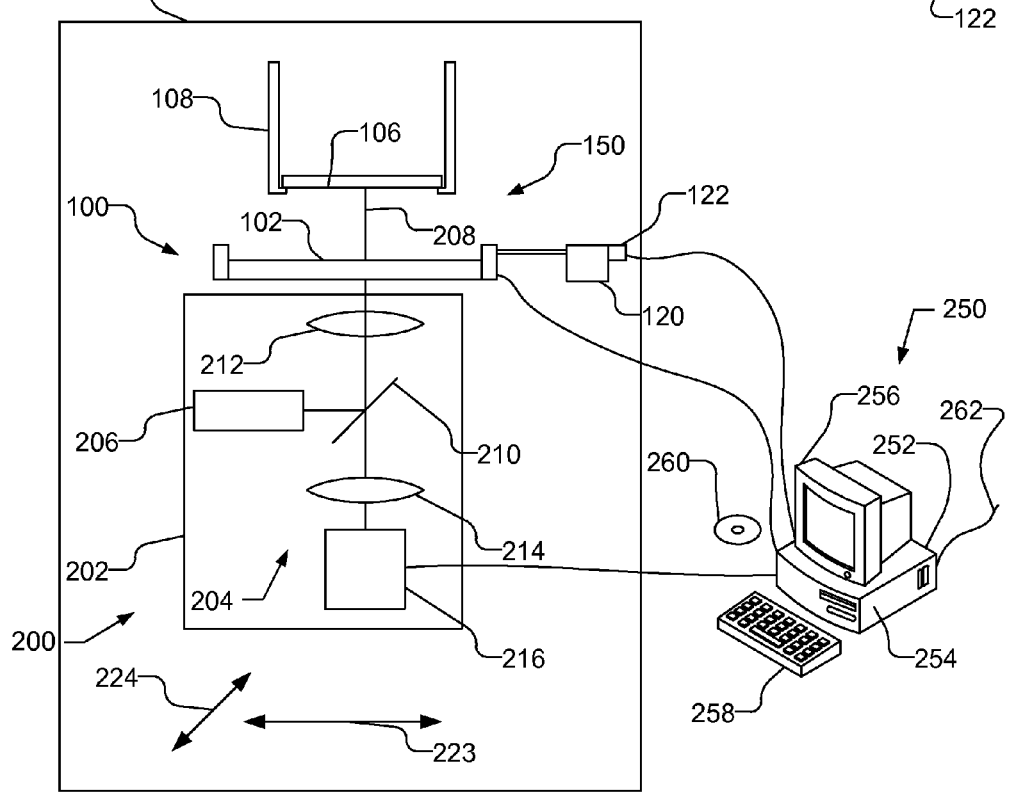
FIG. 4 is a schematic view of a metrology device that may be used with the lens cover plate and purge device and/or heating device.

FIG. 4 is a schematic view of an integrated metrology module 300 which is configured to be attached to a process tool and that includes a metrology device 200 that may be used with the cover plate 102 and purge device 100 and/or heating device 150. Metrology device 200 includes an optics head 202 coupled to a computer 250, such as a workstation, a personal computer, central processing unit or other adequate computer system, or multiple systems. The optical metrology device 200 illustrated in FIG. 4 is, e.g., a spectroscopic reflectometer. If desired, other metrology devices, including single wavelength or spectroscopic devices, may be used with the cover plate 102 and purge device 100 and/or heating device 150, such as ellipsometers, scatterometers, interometers, microscopes, and others. Additionally, if desired, multiple optical heads, i.e., different metrology devices, may be combined in the same metrology device 200. The computer 250 may also control the movement of the optical metrology device 200 or a portion of the optical metrology device 200 in, e.g., Polar (i.e., R and θ) coordinates, or Cartesian coordinates (as illustrated by arrows 224 and 223), using actutators. If desired, the wafer 106 held on a wafer handling system, shown as arms 108, may also or alternatively be moved. The wafer 106, via arms 108, and/or optical head 202 may also be capable of vertical motion, e.g., for focusing.

The optical head 202 may include a broadband light source 206, such as a Xenon Arc lamp and/or a Deuterium lamp, and a detector 216, such as a spectrometer. In operation, light produced by the light source 206 may be directed toward the wafer 106, along optical axis 208 with a beam splitter 210. An objective 212, which may be at least part of the optics 104, shown in FIGS. 1 and 2, focuses the light onto the sample 230 and receives reflected light from the sample 230. The reflective light may pass through the beam splitter 210 and is focused with lens 214 onto the detector 216. The detector 216 provides a spectroscopic signal to the computer 250. The objective 212, beam splitter 210, lens 214, and detector 216 are merely illustrative of typical optical elements that may be used. Additional optical elements, such as a polarizer and/or analyzer, may be used if desired. Moreover, generally, additional optical elements such as field stops, lenses, etc. may be present in the optics 104, shown in FIGS. 1 and 2.

The computer 250 includes a processor 252 with memory 254, as well as a user interface including e.g., a display 256 and input devices 258. The computer 250 may be coupled to control the purge device 100, e.g., via the flow controller 122. The computer 250 may additionally be coupled to receive temperature data from the temperature sensor 154 and to control the heating element 152 in response. Additionally, non-transitory computer-usable storage medium 260 may have computer-readable program code embodied thereon and may be used by the computer 250 for causing the processor to control the metrology device and to perform the functions described herein, including controlling the air flow of the purge device 100, e.g., via the flow controller 122 and/or controlling the heating element 152 via temperature sensor 154 (as illustrated in FIG. 2) and/or adjusting for changes in optical properties of the cover plate 102 due to heating as measured by the temperature sensor 154. The data structures and software code for automatically implementing one or more acts described in this detailed description can be implemented by one of ordinary skill in the art in light of the present disclosure and stored, e.g., on a computer readable storage medium 260, which may be any device or medium that can store code and/or data for use by a computer system such as processor 252. The computer-usable storage medium 260 may be, but is not limited to, magnetic and optical storage devices such as disk drives, magnetic tape, compact discs, and DVDs (digital versatile discs or digital video discs). A communication port 262 may also be used to receive instructions that are stored in memory 254 or other storage in computer 250 and used to program the computer 250 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. An apparatus comprising:
a cover plate or lens positioned over optics of an optical metrology device, wherein the optical metrology device and the cover plate or lens are configured to be below a wafer during measurement of the wafer;
a purge device comprising a ring element extending around a periphery of the cover plate or lens, the ring element comprising a plurality of apertures through which a purge gas or air is expelled over a surface of the cover plate or lens that faces the wafer;
one or more heating elements extending around the periphery of the cover plate or lens that heat the cover plate above a dewpoint temperature of contaminant vapor from the wafer; and
a heat sensor mounted on the cover plate or lens, wherein the heat sensor monitors a temperature of the cover plate to compensate for optical changes to the cover plate due to the temperature during measurement of the wafer by the optical metrology device.

2. The apparatus of claim 1, wherein the plurality of apertures expel the purge gas or air parallel with the surface of the cover plate or lens.

3. The apparatus of claim 1, wherein the one or more heating elements are controlled using the heat sensor.

4. The apparatus of claim 1, wherein the cover plate or lens and the purge device are part of an integrated metrology module.

5. An apparatus comprising:
a cover plate or lens positioned over optics of an optical metrology device, wherein the optical metrology device and the cover plate or lens are configured to be below a wafer during measurement of the wafer;
one or more heating elements extending around a periphery of the cover plate or lens that heat the cover plate above a dewpoint temperature of contaminant vapor from the wafer; and
a heat sensor mounted on the cover plate or lens, wherein the heat sensor monitors a temperature of the cover plate to compensate for optical changes to the cover plate due to the temperature during measurement of the wafer by the optical metrology device.

6. The apparatus of claim 5, wherein the one or more heating elements are controlled using the heat sensor.

7. The apparatus of claim 5, wherein the cover plate or lens and the one or more heating elements are part of an integrated metrology module.

8. An integrated metrology module configured to be attached to a process tool, the integrated metrology module comprising:
an optical metrology device;
a wafer handling system for holding a wafer during measurement of the wafer by the optical metrology device;
a cover plate or lens positioned between optics of the optical metrology device and the wafer held by the wafer handling system during measurement of the wafer by the optical metrology device;
a purge device comprising a ring element extending around a periphery of the cover plate or lens, the ring element comprising a plurality of apertures through which a purge gas or air is expelled over a surface of the cover plate or lens that faces the wafer;
one or more heating elements extending around the periphery of the cover plate or lens that heat the cover plate above a dewpoint temperature of contaminant vapor from the wafer; and
a heat sensor mounted on the cover plate or lens, wherein the heat sensor monitors a temperature of the cover plate to compensate for optical changes to the cover plate due to the temperature during measurement of the wafer by the optical metrology device.

9. The integrated metrology module of claim 8, wherein the plurality of apertures expel the purge gas or air parallel with the surface of the cover plate or lens.

10. The integrated metrology module of claim 8, wherein the one or more heating elements are controlled using the heat sensor.

* * * * *